(12) United States Patent
Boeke et al.

(10) Patent No.: US 10,865,417 B2
(45) Date of Patent: Dec. 15, 2020

(54) YEAST SYNTHETIC BIOLOGY PLATFORM FOR IDENTIFYING SHIKIMATE PATHWAY ENZYME INHIBITORS

(71) Applicants: New York University, New York, NY (US); Neochromosome Inc., Chapel Hill, NC (US); The Johns Hopkins University, Baltimore, MD (US)

(72) Inventors: Jef Boeke, New York, NY (US); Leslie Mitchell, New York, NY (US); Joe De Angelo, Chapel Hill, NC (US); Joel S. Bader, Bronx, NY (US)

(73) Assignees: New York University, New York, NY (US); Neochromosome Inc., Chapel Hill, NC (US); The Johns Hopkins University, Baltimore, MD (US)

(*) Notice: Subject to any disclaimer, the term of this patent is extended or adjusted under 35 U.S.C. 154(b) by 0 days.

(21) Appl. No.: 16/374,827

(22) Filed: Apr. 4, 2019

(65) Prior Publication Data

US 2019/0309314 A1 Oct. 10, 2019

Related U.S. Application Data

(60) Provisional application No. 62/653,600, filed on Apr. 6, 2018.

(51) Int. Cl.

| | | |
|---|---|---|
| *A61P 33/00* | (2006.01) |
| *C12R 1/865* | (2006.01) |
| *C12N 15/81* | (2006.01) |
| *C12N 15/52* | (2006.01) |
| *C12N 15/62* | (2006.01) |
| *C12Q 1/02* | (2006.01) |

(52) U.S. Cl.
CPC ............ *C12N 15/81* (2013.01); *C12N 15/52* (2013.01); *C12N 15/62* (2013.01); *C12Q 1/025* (2013.01); *C12R 1/865* (2013.01); *C12Y 101/01025* (2013.01); *C12Y 205/01019* (2013.01); *C12Y 205/01054* (2013.01); *C12Y 207/01071* (2013.01); *C12Y 402/0101* (2013.01); *C12Y 402/03004* (2013.01)

(58) Field of Classification Search
CPC ........ C12N 15/81; C12N 9/0004; C12N 9/10; C12N 9/88; C12P 5/007
See application file for complete search history.

(56) References Cited

U.S. PATENT DOCUMENTS

2019/0002892 A1* 1/2019 Shao ...................... C12N 15/81

OTHER PUBLICATIONS

Cheung, V. et al., Identification of Polyketide Inhibitors Targeting 3-Dehydroquinate Dehydratase in the Shikimate Pathway of Enterococcus faecalis, PLOS One, Jul. 29, 2014, vol. 9, No. 7, 9 pages.
Mir, R. et al., The shikimate pathway: Review of amino acid sequence, function and three-dimensional structures of the enzymes, Critical Reviews in Microbiology, Aug. 6, 2013, pp. 1-18.
Avitia-Dominguez, C. et al., Inhibition and Biochemical Characterization of Methicillin-Resistant *Staphylococcus aureus* Shikimate Dehydrogenase: An in Silico and Kinetic Study, Molecules, Apr. 10, 2014, vol. 19, No. 4, pp. 4491-4509.
Gonzalez-Bello, C., Inhibition of Shikimate Kinase and Type II Dehydroquinase for Antibiotic Discovery: Structure-Based Design and Simulation Studies, Current Topics in Medicinal Chemistry, 2016, vol. 16, No. 9, pp. 960-977.

* cited by examiner

*Primary Examiner* — Maryam Monshipouri
(74) *Attorney, Agent, or Firm* — Hodgson Russ LLP (57) ABSTRACT

Provided are compositions and methods for compound discovery. Modified yeast that have their endogenous yeast shikimate pathway disrupted or deleted, and replaced with homologous pathway genes from one or more distinct organisms, are provided and used in assays of test agents. The homologous pathway genes are designed to supplement the disrupted or deleted shikimate pathway genes. The assays are designed to identify whether or not the test agents can interfere with the function of enzymes in the shikimate pathway from organisms that are distinct from the yeast avatar hosts. In embodiments, the disruption/deletion of the yeast endogenous shikimate pathway results in the yeast being incapable of producing chorismic acid.

7 Claims, 5 Drawing Sheets
(5 of 5 Drawing Sheet(s) Filed in Color)

Figure 1

A. ID CDSs from source organism (KEGG)
↓
Re-code for optimized yeast expression
↓
Assign yeast regulatory sequences
↓
Design & segment pathway
↓
Order DNA
↓
Assemble pathway
↓
Transform *aro1Δ* yeast strain
↓
Test complementation −Trp,Phe,Tyr

B.

| | *aro1Δ* [empty vector] | *aro1Δ* [shikimate pathway] |
|---|---|---|
| −Trp,Phe,Tyr | − | ? |
| +Trp,Phe,Tyr | + | + |

YEAST SYNTHETIC BIOLOGY PLATFORM FOR IDENTIFYING SHIKIMATE PATHWAY ENZYME INHIBITORS

CROSS REFERENCE TO RELATED APPLICATIONS

This application claims priority to U.S. provisional patent application No. 62/653,600, filed Apr. 6, 2018, the disclosure of which is incorporated herein by reference.

FIELD

The present invention relates generally to modified fungi such as yeast that are suitable for screening compounds to determine if the compounds affect the multi-enzyme shikimate pathway, and for identifying components of the multi-enzyme pathway.

BACKGROUND

The rise of drug resistant microorganisms and the emergence of new pathogens together pose an enormous threat to human health and security. There is a desperate need to identify new antimicrobial compounds and their molecular targets. While high-throughput screens to identify antimicrobials are possible for many pathogens, on the whole screens are cumbersome because of biosafety requirements and the need to establish organism-specific assays amenable to high-throughput automation, a challenge for slow growing organisms like *Mycobacterium tuberculosis* or for difficult-to-culture pathogens such as apicomplexans. Thus, there is an ongoing and unmet need for alternatives to existing approaches to identify compounds that are candidates for use as antimicrobial agents, and for compounds that can target other unwanted organisms. The present disclosure is pertinent to this need.

SUMMARY

The present disclosure provides compositions and methods that relate to cell-based platforms for compound discovery. The disclosure provides in certain aspects modified yeast that have the endogenous yeast shikimate pathway disrupted or deleted, and replaced with homologous pathway genes from one or more distinct organisms. In embodiments, the disruption/deletion of the yeast endogenous shikimate pathway results in the yeast being incapable of producing chorismic acid. The modified yeast are accordingly considered to be avatars that are useful for, among other purposes, screening test agents to assess the effects of the agents on proteins encoded by the homologous genes. Thus, embodiments of the disclosure facilitate, for example, pathogen DNA sequence to yeast-based pathway screens. In embodiments, the disclosure provides approaches to identify useful compounds, such as broad-spectrum anti-infective agents. Among other advantages, the disclosure provides for high-throughput screening of any of a wide variety of test agents, removing the need to work directly with pathogenic organisms, and the capability to analyze pathways from pathogens or other organisms that pose difficult challenges to lab-based culturing.

In view of the foregoing, it will be apparent to those skilled in the art that the present disclosure provides in one aspect a modified yeast comprising genomic modification(s) which comprise a disruption and/or deletion of all or a segment of least one endogenous gene that encodes a shikimate pathway enzyme. In embodiments, the disruption and/or deletion of all or a segment of least one endogenous gene that encodes a shikimate pathway enzyme is directed to at least one gene that encodes at least one of the following enzymes: DAHPS, 3-deoxyarabinoheptulosonate-7-phosphate synthase; DHQS, dehydroquinate synthase; DHQD, dehydroquinate dehydratase; SDH, shikimate dehydrogenase; SHK, shikimate kinase; EPSPS, 5-enolpyruvyl shikimate-3-phosphate synthase; or chorismate synthase. In embodiments, the endogenous yeast gene that is disrupted or deleted is selected from the group consisting of ARO1, ARO2, ARO3 and ARO4, and combinations thereof.

The yeast are engineered such that they contain at least one supplemental gene which encodes a heterologous enzyme that is homologous to the disrupted and/or deleted endogenous yeast gene. One or more supplemental genes can be used, and can originate in one, or more than one, distinct organisms. In certain embodiments, the supplemental gene is homologous to the endogenous yeast gene that is disrupted or deleted and is from a species that is infectious to mammals, insects, birds, fish or plants, or is from a prokaryotic pathogen, or is from a eukaryotic pathogen.

The supplemental gene(s) restore biosynthesis of chorismic acid to the modified yeast. In certain embodiments, the supplemental gene is present on an episomal element. The episomal element may contain a selectable marker, and/or may contain an essential gene of the yeast that is distinct from the gene encoding the endogenous yeast shikimate pathway enzyme. In the latter configuration, the essential yeast gene can be relocated from a chromosome of the yeast to the episomal element.

In another aspect, the disclosure provides a method for identification of a test agent that can inhibit one or more enzymes that are part of the shikimate pathway. The method comprises introducing the test agent into modified yeast as described above, wherein an inhibition of growth of the modified yeast relative to a control is indicative that the test agent inhibits one or more of the shikimate pathway enzymes. This approach is suitable for multiplex and high throughput approaches, and for testing a single agent, small sets of agents, and large numbers of distinct agent.

DESCRIPTION OF THE FIGURES

The patent or application file contains at least one drawing executed in color. Copies of this patent or patent application publication with color drawing(s) will be provided by the Office upon request and payment of the necessary fee.

FIG. 1. Schematic of the conserved shikimate pathway. Four yeast genes, ARO3, ARO4, ARO1, and ARO2, encode seven shikimate pathway enzymatic activities. The end product of the pathway is chorismic acid, also known as chorismate, which is essential for yeast growth in culture medium lacking one or more of the aromatic amino acids (tryptophan, phenylalanine, tyrosine). The enzymatic function encoded by the yeast genes ARO3 and ARO4 is DAPHS. The enzymatic functions encoded by the pentafunctional yeast ARO1 gene are shown in red, and include DHQS, DHQD, EPSPS, and SHK. The enzymatic function encoded by the yeast gene ARO2 is chorismate synthase. Abbreviations are defined as follows: DAHPS, 3-deoxyarabinoheptulosonate-7-phosphate synthase (EC 2.5.1.54); DHQS, ehydroquinate synthase (EC 4.2.3.4); DHQD, dehydroquinate dehydratase (EC 4.2.1.10); SDH, shikimate dehydrogenase (EC 1.1.1.25); SHK, shikimate kinase (EC 2.7.1.71); EPSPS, 5-enolpyruvyl shikimate-3-phosphate synthase (EC 2.5.1.19); chorismate synthase (EC 4.2.3.5).

FIG. 3. Yeast avatar complementation and glyphosate sensitivity assays. Yeast avatars encode the shikimate pathway of the indicated organisms on a neochromosome as follows: Sce, *Saccharomyces cerevisiae*; Sau, *Staphylococcus aureus*; Ftu, *Francisella tularensis*; Ype, *Yersinia pestis*; Mtu, *Mycoplasma tuberculosis*; Xfa, *Xylella fastidiosa*; Pmi, *Proteus mirabilis*; Kpn, *Klebsiella pneumonia*; Rso, *Ralstonia solanacearum*; Aba, *Acinetobacter baumannii*; Fga, *Fusarium graminearum*; Hin, *Haemophilus influenzae*; Lpn, *Legionella pneumophila*; Ngo, *Neisseria gonorrhoeae*; Pae, *Pseudomonas aeruginosa*. HGC and LGC indicate two versions of the pathway built with terminators with high GC or low GC content, respectively. All avatar neochromosomes as well as an empty vector control ([empty]) are carried in a *S. cerevisiae* strain lacking the ARO1, encoding 5 enzymatic activities of the shikimate pathway encompassing steps 2-6 (see FIG. 1). A strain encoding wild-type ARO1 and carrying an empty vector was also tested (ARO1+ [empty]). Ten-fold serial dilutions of each strain were grown for 6 days at 30° C. on drop-in medium (adding back only the required amino acids histidine, methionine and leucine) along with the three aromatic amino acids (AAA; tryptophan, phenylalanine, tyrosine) where indicated. 0.25% glyphosate (vol/vol of a commercially available 41% solution of glyphosate) was added to the plates where indicated.

FIG. 4. N-1 assay to determine function of individual enzymatic activities of heterologous pathways that do not complement. (A) Schematic of the N-1 assay. (B) Yeast cells lacking ARO1 (aro1Δ) and transformed with one of four non-complementing pathways (*Arabidopsis thaliana*, [Ath]; *Candida albicans*, [Cal]; *Plasmodium falciparum*, [Pfa]; *Toxoplasma gondii*, [Tgo]) were co-transformed with a full-length *Staphylococcus aureus* pathways ([Sau HGC]), one of five derivatives of [Sau HGC] lacking a single enzymatic activity (step 2, step 3, step 4, step 5, step 6), or an empty vector (empty) lacking all shikimate pathway enzymatic activities. Cells were plated on replete medium including aromatic amino acids (+AAA) or selective medium lacking aromatic amino acids (-AAA). Cell growth formation indicates complementation and absence of cell growth indicates no complementation. Conclusions of the N-1 assay are indicated.

FIG. 5. Yeast avatar complementation for step 1 of the shikimate pathway. Yeast cells lacking ARO3 and ARO4 (aro3Δ aro4Δ) were transformed with heterologous shikimate pathways encoding enzymatic activities for the first six steps of the pathway (*Francisella tularensis*, [Ftu HGC]; *Chlamydia psittaci*, [Cps-LGC] or [Cps-HGC]; *Arabidopsis thaliana*, [Ath]; empty vector, [empty]). Cells were plated on replete medium including aromatic amino acids (+AAA) or selective medium lacking aromatic amino acids (-AAA). Cell growth indicates complementation and absence of cell growth indicates no complementation.

FIG. 6. Molecular target identification of the shikimate pathway inhibitor glyphosate in the yeast avatar system. Yeast cells lacking ARO1 (aro1Δ) carrying the *Neisseria gonorrhoeae* pathway ([Ngo]) or an empty vector (empty) were co-transformed with a full-length *Staphylococcus aureus* pathways ([Sau HGC]), one of five derivatives of [Sau HGC] lacking a single enzymatic activity (step 2, step 3, step 4, step 5, step 6), or an empty vector (empty) lacking all shikimate pathway enzymatic activities. Cells were plated on replete medium including aromatic amino acids (+AAA) or selective medium lacking aromatic amino acids (-AAA). 0.25% glyphosate (vol/vol of a commercially available 41% solution of glyphosate) was added to the plates where indicated. Cell growth indicates complementation and absence of cell growth indicates no complementation.

DETAILED DESCRIPTION

Unless defined otherwise, all technical and scientific terms used herein have the same meaning as commonly understood by one of ordinary skill in the art to which this invention belongs.

Every numerical range given throughout this specification includes its upper and lower values, as well as every narrower numerical range that falls within it, as if such narrower numerical ranges were all expressly written herein.

The disclosure includes all proteins and contiguous segments of them described herein, all polynucleotides, and complementary and reverse-complementary sequences thereof.

The present disclosure provides novel, cell-based platforms for compound discovery. The approach is focused on the shikimate pathway that exhibits the following properties: (i) inhibition of the pathway causes microorganism (or other organism) growth inhibition or death; (ii) conservation in structure across species to provide useful antimicrobial spectrum; and (iii) structural differences or even absence from human cells to avoid mechanism-based toxicity.

In embodiments, the present disclosure provides modified yeast, as further described below. In embodiments, the yeast is a *Saccharomyces*, such as *Saccharomyces cerevisiae*. In various implementations the disclosure provides bespoke yeast "avatars" for screening against proteins expressed from heterologous gene sequences that are endogenous to pathogens, or other unwanted organisms, or any organism of interest. It is expected that these engineered cells will permit standardized, systematic sequence-to-screen approaches for anti-infective discovery, and analysis of test compounds for other purposes as described herein, going directly from pathogen DNA sequence to yeast-based pathway screens. Additional validation can be performed if desired using the actual organism from which shikimate pathway genes are adapted. The biological framework described herein can include a built in counter-screen against general yeast toxins and a mechanism to distinguish broad- and narrow-spectrum antibiotics.

For use in the assays of this disclosure that are described further below, a modified yeast is used. In certain embodiments, the modified yeast comprises genomic modification(s) comprising disruption and/or deletion of all or a segment of least one endogenous shikimate pathway gene. In embodiments, such disruptions/deletions result in rendering the yeast incapable of producing chorismic acid. In embodiments, the heterologous genes encoding shikimate pathway enzymes functionally complement the disrupted/deleted shikimate pathway genes, meaning they enable biosynthesis of chorismic acid. In embodiments, the heterologous genes code for enzymes that are homologous to the proteins encoded by the endogenous genes, but are from a distinct organism. The modified yeast thus comprise heterologous shikimate pathway genes, which are also referred to herein as supplemental genes. "Endogenous" means the shikimate genes are present on an unmodified chromosome of a yeast. "Heterologous" means one or more shikimate pathway genes that are not present in chromosomes of unmodified yeast.

As noted above, the heterologous genes code for proteins that are homologous to the proteins encoded by the endogenous yeast genes. "Homologous" means the shikimate pathway gene(s) encode enzyme(s) that perform the same or similar function as the proteins encoded by the endogenous yeast shikimate pathway genes. Those skilled in the art can readily determine whether or not any particular gene encodes a protein that is homologous to a protein encoded by another gene. Further, functional complementation in the modified yeast strain for the biosynthesis of chorismic acid indicates the gene(s) encoding the protein is homologous. In embodiments, the homologous gene that is expressed in the modified yeast codes for a protein that is from 50-100% identical to the protein expressed in the original, distinct organism. Homology may be, for example, across the entire length of the protein, or may be limited to one or more functional domains of the protein. Yeast modified according to this disclosure accordingly comprise supplemental shikimate pathway genes from organisms that are not the same species as the modified yeast.

In embodiments, the endogenous shikimate pathway proteins encoded by the gene(s) that is/are disrupted or deleted in the modified yeast, any one or combination of which may be replaced with a homologous gene from a different organism as described herein, are selected from the group of genes consisting of genes encoding the following enzymatic functions in *S. cerevisiae*: DAHPS, 3-deoxyarabinoheptulosonate-7-phosphate synthase (EC 2.5.1.54); DHQS, dehydroquinate synthase (EC 4.2.3.4); DHQD, dehydroquinate dehydratase (EC 4.2.1.10); SDH, shikimate dehydrogenase (EC 1.1.1.25); SHK, shikimate kinase (EC 2.7.1.71); EPSPS, 5-enolpyruvyl shikimate-3-phosphate synthase (EC 2.5.1.19); chorismate synthase (EC 4.2.3.5), and combinations thereof.

In embodiments, the disclosure uses modified yeast that comprise a disruption or deletion of any one or a combination of gene is selected from the group consisting of ARO1, ARO2, ARO3 and ARO4, and combinations thereof. Each of these yeast genes is known in the art, and their nucleotide sequences can be readily identified. Further, each of these genes is identified herein by its Kyoto Encyclopedia of Genes and Genomes (KEGG) reference number. KEGG is a publicly accessible database, available at genome.jp/kegg/. Each KEGG reference number can be used to access the nucleotide sequences of the yeast genes, as well as homologous genes from many different organisms. All polynucleotide sequences and all protein sequences associated with the KEGG "EC" numbers of this disclosure are incorporated by reference herein, as they exist on the filing date of this application or patent. Those skilled in the art will also recognize that additional entries for homologous genes may be entered into the KEGG database from time to time, and can be analyzed for use in embodiments of this disclosure. In embodiments, the homologous genes from distinct organisms that are used to modify yeast as described herein can be codon-optimized before being introduced into the yeast. In embodiments, the homologous gene(s) are introduced into the yeast, or are otherwise configured, such that the homologous gene is present on an episomal element. In embodiments, the episomal element optionally comprises a selectable marker, and/or an essential gene of the yeast that is distinct from the genes encoding the endogenous yeast shikimate pathway enzymes, and that has been relocated from a chromosome of the yeast to the episomal element. Compositions and methods for introducing supplemental genes, such as onto episomal elements, for disrupting endogenous genes, and for relocating genes from a native chromosome to an episomal element, are known in the art and can be adapted to implement embodiments described herein by those skilled in the art when provided the benefit of this disclosure.

In more detail, a yeast-based drug screening system of this disclosure is believed to be differentiated from existing yeast drug-screening platforms by expressing unique enzymatic activities of the shikimate metabolic pathway that together provide an essential function in yeast. Each enzymatic activity represents a unique druggable target. By screening at the pathway level, this effectively multiplexes the screen compared with a biochemical assay developed for an individual target. Pathway-level multiplexing targeting the shikimate pathway increases the chances of identifying hits in a drug screen by up to seven-fold. Thus, there is strong potential to identify useful compounds, which can include but are not necessarily limited to broad-spectrum anti-infective agents. Further, the disclosure allows for testing species-specificity of an identified compound using a series of yeast avatars, each expressing an enzymatic pathway transplanted from a different pathogen or other organism of interest. A yeast strain lacking its native, homologous pathway, by disrupting or deleting one or more genes that are required for pathway function, provides a counterscreen against off-target yeast cytotoxicity. Other advantages of the present disclosure include but are not necessarily limited to enabling high-throughput screening, avoiding the handling of pathogenic organisms, the ability to screen using pathways from pathogens or other organisms that are difficult to impossible to culture in the lab (e.g. parasites), the test candidate compound screen hits will be specific to the engineered shikimate pathway, and resistance mechanisms can be readily identified via drug selection and sequencing of metabolic pathways encoded by genetic elements from survivors.

The shikimate pathway is known in the art. It is composed of seven enzymatic steps (FIG. 2) and links central carbon metabolism to the production of aromatic amino acids. Enzymes of this pathway may be targets for new antibiotics (8). For instance, knockout mutations of 5-enolpyruvyl shikimate-3-phosphate synthase (EPSPS) in both Gram negative and Gram positive bacteria were found to lead to attenuation of bacterial virulence, consistent with the utility of this targeting approach (9). Fluorinated analogues of shikimate blocked the growth of *Plasmodium falciparum*, suggesting the shikimate pathway as a valid target for new anti-parasitic agents (10). Glyphosate, the active ingredient in the herbicide sold under the tradename ROUNDUP®, kills plants by inhibiting EPSPS and plants engineered for resistance carry a glyphosate-insensitive form of the enzyme (7). Compounds that inhibit enzymes of the *Mycoplasma tuberculosis* shikimate pathway have been characterized (11-14) and related analysis has been performed on organisms that include *Staphylococcus aureus* (15), *Helicobacter pylori* (16), and *Enterococcus faecalis* (17).

While the lack of growth when the shikimate pathway is targeted is due in part to the inability to synthesize aromatic amino acids, the shikimate pathway is also linked to other metabolic networks and thus the efficacy of compounds targeting this pathway may be even greater than expected for simple starvation for lack of amino acids. Some evidence suggests that compounds targeting the shikimate pathway may be expected to induce stasis rather than cell death (i.e. bacteriostatic vs. bacteriocidal). Specifically, shikimate pathway mutants have been used to construct attenuated mutants of *S. typhimurium*, *Salmonella typhi*, *Shigella flexneri*, *Pasteurella multocida*, and *A. salmonicida* that can be exploited as live vaccines (18-24). In the absence of chorismate (and downstream molecules) the organism may scavenge aromatic amino acids from host cells to prevent immediate death, or via a starvation response may simply stop growing but not die. In the case of an infectious organism, this could allow the immune system of a host to mount an antibody-mediated response, resulting in clearance of the infection and also preventing future reinfection. Further, this outcome would avoid the absolute selective pressure associated with outright death, reducing emergence of early arising drug resistant strains. Further, the invention is not necessarily limited to testing candidates for use as antibiotics because it can be adapted, given the benefit of this disclosure, to identify agents that can function as herbicides and insecticides, or for use against any organism for which the shikimate pathway is essential to viability. Thus, it is considered that the disclosure can be used to identify, for example, test agents/compounds that affect shikimate pathways for a wide variety of pathogenic and/or destructive or otherwise unwanted organisms, such as pathogenic prokaryotes, and/or invasive species of any type that rely on the shikimate pathway, and/or parasites that rely on the shikimate pathway that can infect humans and/or non-human mammals. Non-human mammals include but are not limited to domesticated companion mammals, such as felines and canines, and agriculturally important animals, such as cattle, pigs and horses, and also for avian animals, such as agriculturally important fowl, and also for aquatic animals, including but not necessarily limited to agriculturally and/or environmentally important fish and shellfish. The disclosure can also be used to test compounds for activity against shikimate pathway enzymes in photosynthetic organisms, such as algae, and multicellular plants, including but not necessarily limited to invasive and/or otherwise unwanted plants such as weeds, and any organism that is parasitic or otherwise deleterious to multicellular plants.

Figure 4:
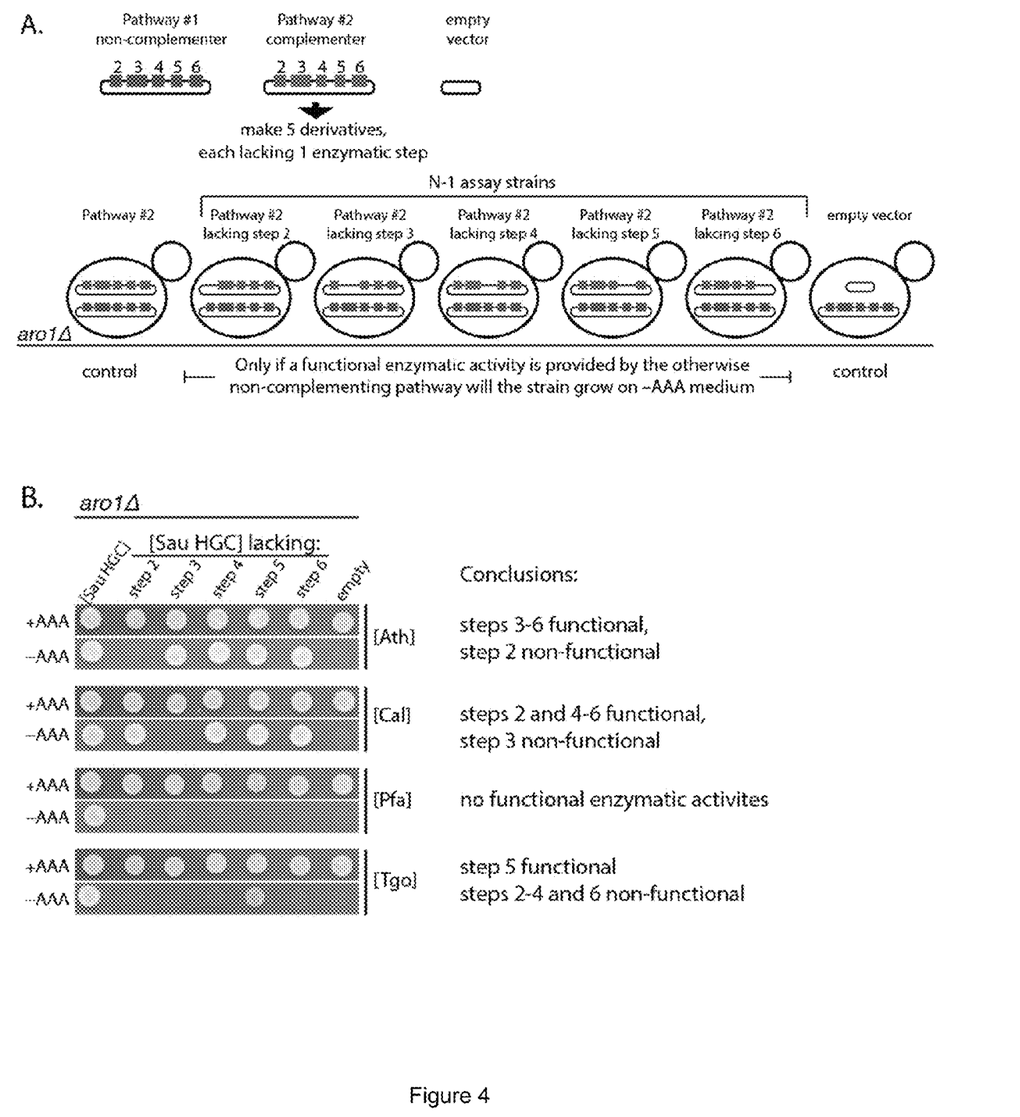
Figure 5:
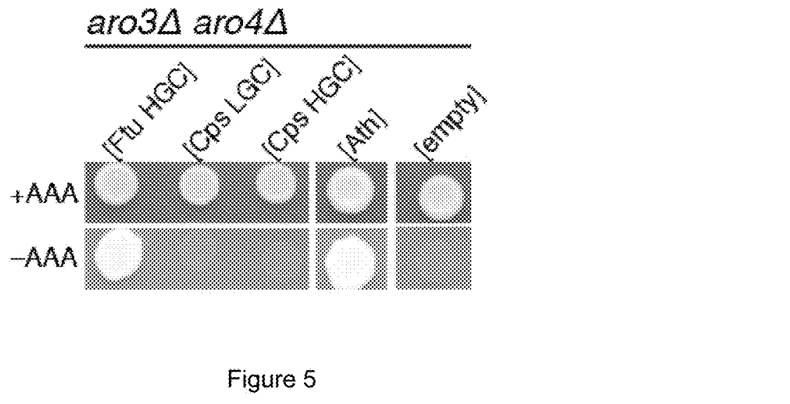

In embodiments, the disclosure provides for determining whether or not the homologous genes and/or the proteins encoded by the genes are functional in the yeast avatars, such as illustrated by Examples 2 and 3, and FIGS. 4 and 5, respectively. These examples also support the use of combinations of distinct homologous genes from distinct organisms in the same yeast avatar.

In embodiments, the disclosure provides for determining which particular genes/proteins are the target(s) of test agents. This is demonstrated, for example, in Example 4 and FIG. 6.

In embodiments, this disclosure provides for determining which particular genes/proteins are functional or non-functional in yeast. This is demonstrated, for example, in Example 2 and FIG. 4.

The disclosure is readily scalable for high-throughput approaches, which magnify the multiplex target screening capacity, and can be automated. The disclosure thus provides for concurrent assessment of the effects of many test agents against a plurality of distinct shikimate pathways, thereby facilitating simultaneous evaluation of thousands of interactions between test agents and shikimate pathways taken from a diversity of organisms. Accordingly, the disclosure is suitable for simultaneously testing and identifying agents that have antimicrobial properties, anti-parasite properties (where the parasite may be prokaryotic or eukaryotic), herbicidal compounds, as well as compounds that could have effects against, for example, organisms that have a commensal relationship with the host. For instance, a compound that can selectively target a shikimate pathway that is present in a pathogenic bacteria, but is not present or is less effected by the compound in a non-pathogenic and/or commensal bacteria, could be of particular usefulness.

In embodiments a method of this disclosure comprises adding at least one test agent to a culture of modified yeast cells, wherein the cells express a heterologous shikimate pathway. If desired, the culture of cells can be incubated for a period of time to assess one or more phenotypes, such as a growth phenotype, before adding the test agent. Generally, the cell culture comprising the modified fungus, such as yeast, and the test agent may be incubated together for a period of time. The incubations can be performed for any desirable amount of time, such as from at least one minute, to at least 1-16 hours, including all time values there between to the minute, and all ranges there between, or over a period of at least one to several days. The incubation can be performed at any desirable temperature, with any other controllable conditions, such as controlled humidity, air flow, oxygen content, and the like. The cell culture can be a liquid or solid medium or semi-solid medium, such as a liquid cell culture, or semi-solid culture medium of the type used in a petri or other culture dish. In embodiments, the cell culture comprises a liquid culture or semi-solid medium which is separated into a plurality of reaction chambers, such as in a high-throughput configuration. In an embodiment, the plurality of reaction chambers comprises up to or at least 384 reaction chambers. Into each reaction chamber a distinct test agent may be added, and a change in the cell culture due to the presence of the test agent can be observed. In alternative embodiments, a plurality of culture plates can be used, and individual yeast colonies can be assayed with distinct test agents, the effects of which can be assessed using any suitable technique, such as by human or automated inspection for visually detectable differences in, for example, colony size and/or cell morphology. In an embodiment, a change in the growth of the modified yeast identifies the test agent as a modulator of the heterologous shikimate pathway. In an embodiment, inhibition of growth and/or lethality of the modified yeast indicates the test compound inhibits the function of at least one enzyme that is part of the heterologous shikimate pathway. Any measurement of the effect of a test compound on modified yeast as described herein can be compared to any suitable control. In an embodiment, the control comprises a modified yeast wherein the endogenous shikimate pathway is disrupted/deleted, but wherein endogenous pathway genes are not supplemented with a homologous shikimate pathway counterparts from a distinct organism. In embodiments the control comprises a culture to which a test agent has not been added. In embodiments, the control comprises a culture to which a compound with a known effect has been added. In embodiments, the control comprises a culture to which has been added (or has not been added) one or more compounds that are essential for growth of a modified yeast, such as amino acids.

The following specific examples are provided to illustrate the invention, but are not intended to be limiting in any way.

Example 1

This example provides a demonstration of a plurality of modified *S. cerevisiae* strains, and use of the strains for analyzing the effects of a representative test compound.

Figure 1:
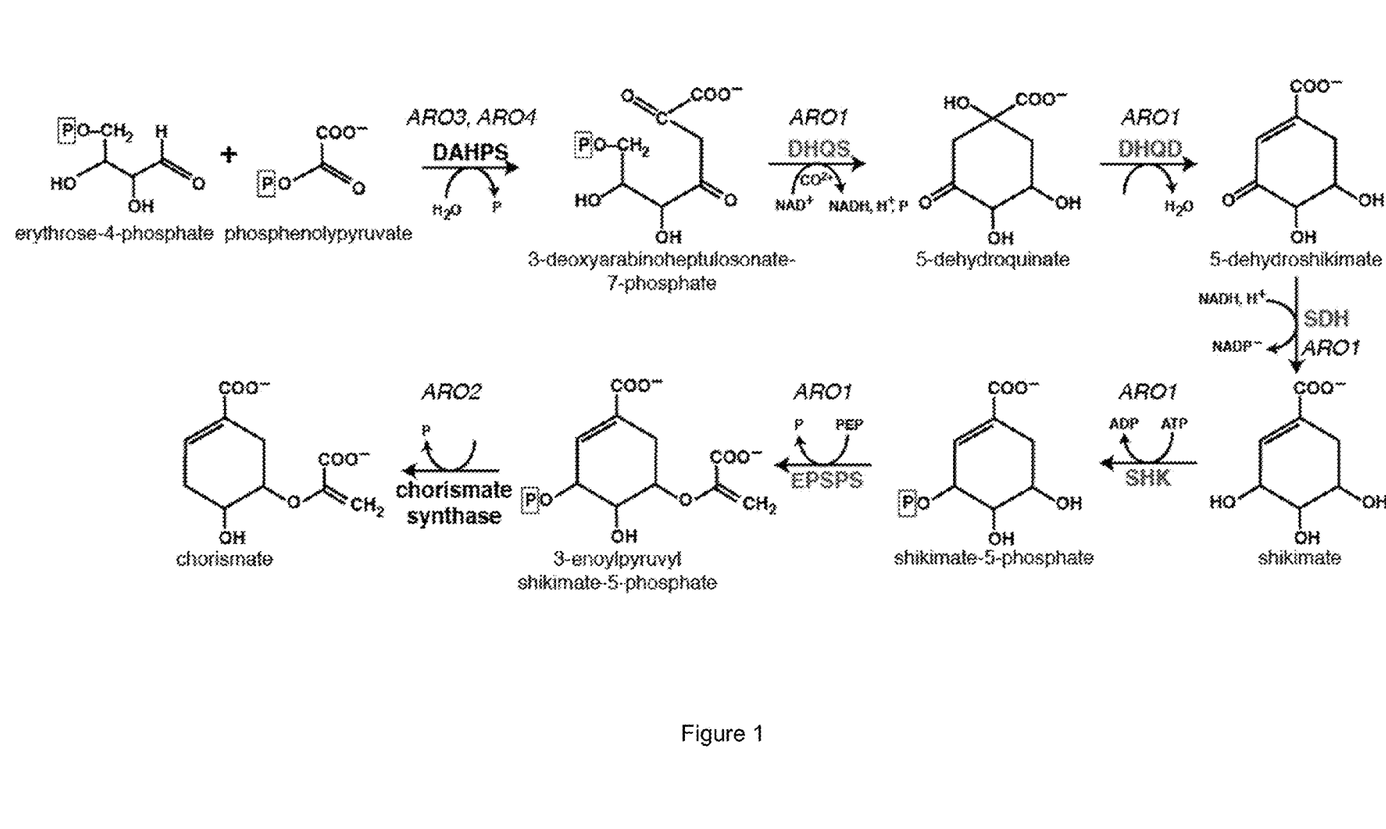
Figure 2:
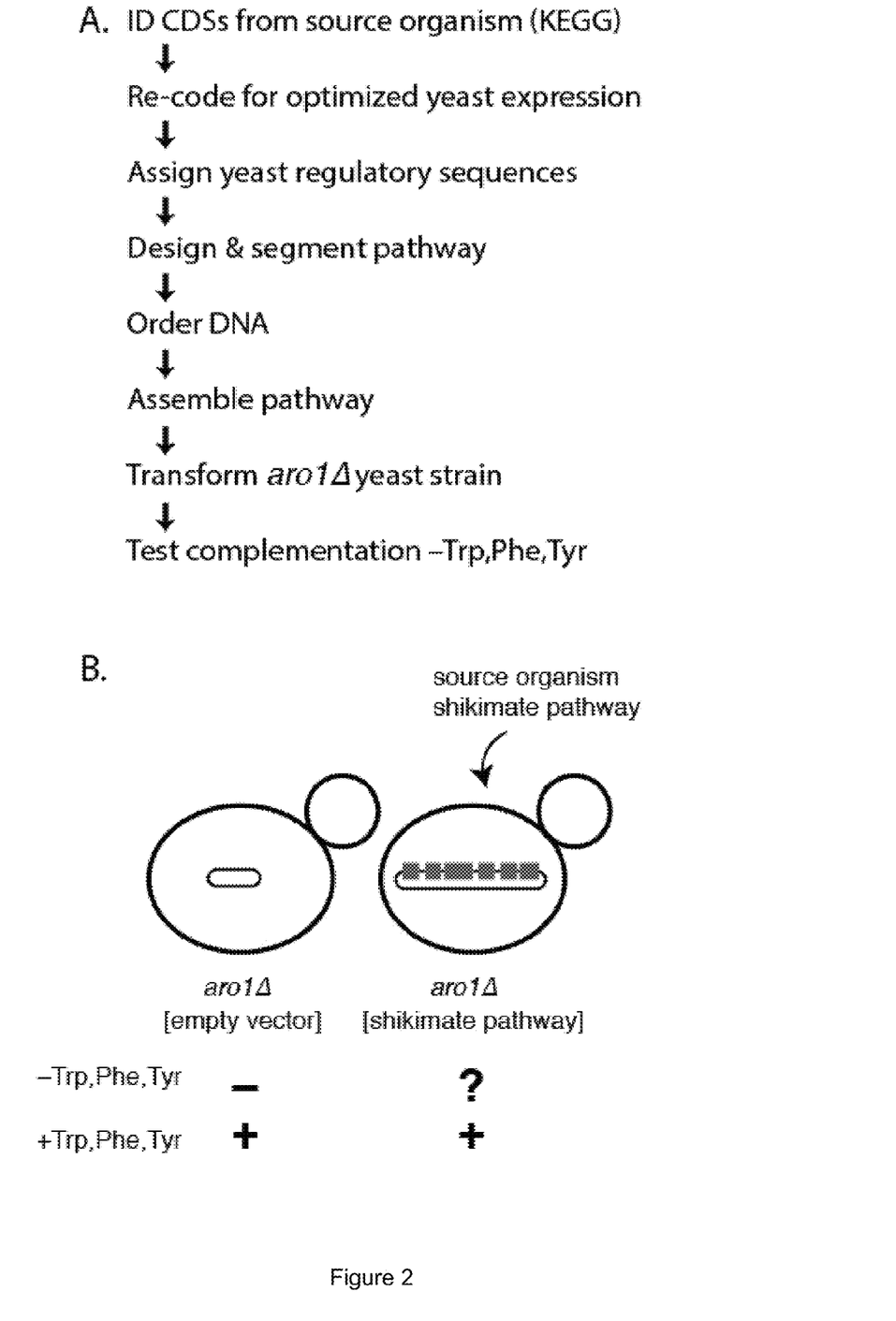
FIG. 2. Pathway design and testing. (A) Project workflow. (B) Schematic of complementation assay.
Figure 3:
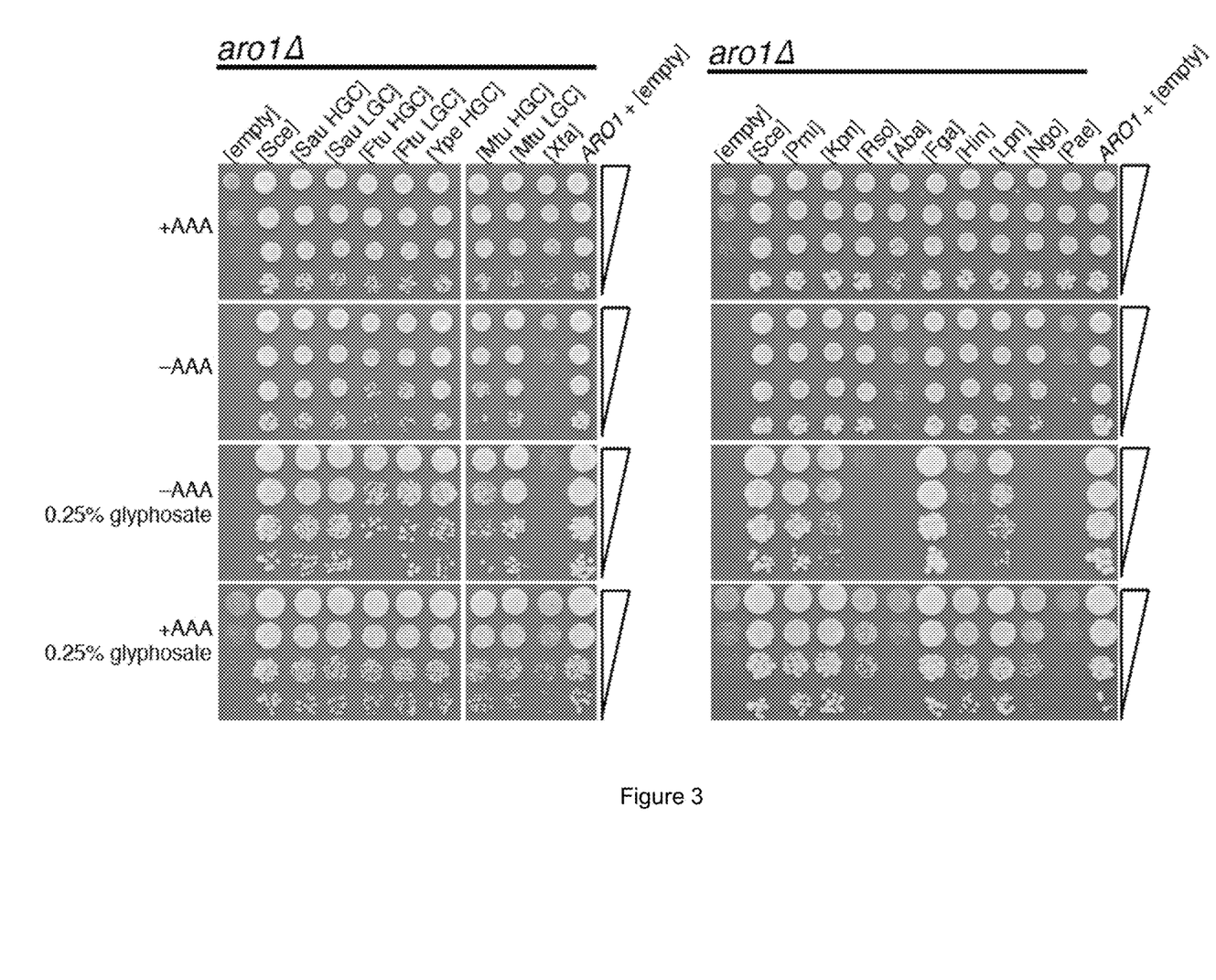

In this representative modified yeast, most of the endogenous shikimate pathway, a single gene encoding the pentafunctional protein ARO1, is deleted (FIG. 1, 2). The aro1Δ yeast strain grows normally on medium replete with aromatic amino acids, but cannot survive on medium lacking them (FIG. 3). Into this strain was transplanted shikimate pathways derived from a diversity of organisms, including but not limited to human and plant pathogenic organisms, to generate avatar strains (Table 1). The non-native (heterologous) pathways have been redesigned for expression in yeast as described above. To evaluate function, aro1Δ yeast cells expressing the non-native engineered pathways were tested for their ability to grow on medium lacking aromatic amino acids (FIG. 3). In most cases the strains grew, indicating the enzymes of the heterologous shikimate pathways provided the required enzymatic activities to produce aromatic amino acids in yeast, a function that is otherwise absent from the strain. Growth in this assay is consistent with the highly conserved function of the enzymatic activities in this pathway. Those skilled in the art will be able to adapt this demonstration in order to test a wide variety of shikimate pathways from distinct organisms against any number of test compounds.

Upon supplementation of the three aromatic amino acids tryptophan, phenylalanine, and tyrosine, glyphosate sensitivity was overcome, indicating specificity of action of the drug in yeast against homologous targets.

Example 2

This example illustrates a strategy to individually analyze enzymatic activity of heterologous shikimate pathways that do not complement aro1Δ yeast cells plated on medium lacking aromatic amino acids.

As discussed above, five steps of the endogenous shikimate pathway are provided by a single gene, ARO1, which encodes a penta-functional protein (FIG. 1, 2). When heterologous shikimate pathways that are designed for expression in yeast (FIG. 2) do not complement aro1Δ yeast cells plated on medium lacking aromatic amino acids, it could be the result of one, two, three, four or all five of the encoded

TABLE 1

Source organisms for shikimate pathway transplantation

| Organism | Description/Disease | NIH/NIAID Pathogen Class | WHO priority level | # genes | Status |
| --- | --- | --- | --- | --- | --- |
| Staphylococcus aureus | Gram-positive/sepsis | Emerging | 2 | 7 | Complements* |
| Francisella tularensis | Gram-negative/tularemia | A | — | 7 | Complements* |
| Yersinia pestis | Gram-negative/plague | A | — | 7 | Complements* |
| Mycobacterium tuberculosis | Gram-positive/negative/TB | C | —** | 7 | Complements* |
| Xylella fastidiosa | Gram-positive/plant pathogen | n/a | n/a | 5 | Complements* (weakly) |
| Proteus mirabilis | Gram-negative/nosocomial | — | 1 | 7 | Complements* |
| Klebsiella pneumonia | Gram-negative/pneumonia | — | 1 | 13 | Complements* |
| Ralstonia solanacearum | Gram-negative/plant pathogen | n/a | n/a | 7 | Complements* |
| Acinetobacter baumannii | Gram-negative/nosocomial | — | 1 | 7 | Complements* (weakly) |
| Fusarium graminearum | Fungus/plant pathogen | n/a | n/a | 1 | Complements* |
| Haemophilus influenzae | Gram-negative/meningitis | — | 3 | 7 | Complements* |
| Legionella pneumophila | Gram-negative/legionellosis | — | — | 7 | Complements* |
| Neisseria gonhorroeae | Gram-negative/gonorrhea | — | 2 | 7 | Complements* |
| Pseudomonas aeruginosa | Gram-negative/nosocomial | — | 1 | 8 | Complements* (weakly) |
| Arabidopsis thaliana | Plant model organism | n/a | n/a | 6 | #Noncomplementer |
| Chlamydia psittaci | Gram-negative/psittacosis | B | — | 5 | #Noncomplementer |
| Toxoplasma gondii | Parasitic alveolate/toxoplasmosis | — | — | 1 | #Noncomplementer |
| Candida albicans | Pathogenic yeast/nosocomial | — | — | 1 | #Noncomplementer |
| Plasmodium falciparum | Parasitic alveolate/malaria | — | — | 1 | #Noncomplementer |

*Complements deletion of the yeast ARO1 gene, encompassing steps two through six of the seven-step shikimate pathway.
Does not complement deletion of the yeast ARO1 gene, encompassing steps two through six of the seven-step shikimate pathway.
**Mycoplasma tuberculosis was not included on the WHO priority pathogens list as it is already recognized globally as a priority.
— not on the list.

Glyphosate is a known inhibitor of EPSPS, the sixth enzyme in the shikimate pathway (7). A panel of yeast avatars was tested for ability to grow on glyphosate (FIG. 3). Under the conditions tested, it was discovered that a number of yeast avatars were sensitive to the drug under the conditions tested, indicating inhibition of the EPSPS enzyme.

heterologous enzymatic activities being non-functional in yeast. To distinguish between these possibilities and determine whether any of the heterologous enzymatic activities are functional in yeast, the "N−1" assay can be used. In this assay, five derivatives of a pathway that is known to complement aro1Δ yeast cells when plated on medium lacking aromatic amino acids (e.g. *Staphylococcus aureus*, Sau) can be made, each lacking a single gene encoding one enzymatic activity. As a result of the gene deletion, none of the derivative N-1 pathways will be able to complement aro1Δ yeast cells when plated on medium lacking aromatic amino acids. The five derivative N-1 pathways are transformed into aro1Δ yeast cells carrying the non-complementing pathway. Each of the five strains can then be evaluated for complementation on medium lacking aromatic amino acids. Only if a functional enzymatic activity is provided by the otherwise non-complementing pathway is it expected that one of the five strains will grow on medium lacking aromatic amino acids. For example, in the absence of step 2 in the N-1 pathway, only if non-complementing pathway step 2 functions will the strain grow on selective medium. The N-1 assay was used to test individual enzymatic activity of four non-complementing pathways (Table 1): *Arabidopsis thaliana*, *Candida albicans*, *Plasmodium falciparum*, and *Toxoplasma gondii* (FIG. 4). In each case at least one non-functional enzyme was identified. For *Arabidopsis thaliana* and *Candida albicans* only a single enzyme was non-functional, while for *Plasmodium falciparum* none of the five enzymatic activities were found to be functional and for *Toxoplasma gondii* only step 5 complemented. Accordingly, based on an approach such as that described in this Example, the disclosure provides for determining whether one or more heterologous genes are responsible for a lack of complementation.

Example 3

This example provides evidence of complementation of heterologous step 1 enzymatic activity in yeast.

A yeast strain lacking ARO3 and ARO4 (aro3Δ aro4Δ) was built by deleting these two genes using standard homologous recombination-dependent methods with selectable markers. The aro3Δ aro4Δ can no longer grow on medium lacking aromatic amino acids since the first step of the shikimate pathway is no longer present (FIG. 1). Into this strain was transformed heterologous shikimate pathways encoding steps 1-6 of the shikimate pathway (FIG. 1). Function of the step 1 enzymatic activity in these heterologous shikimate pathways was interrogated by evaluating growth on medium lacking aromatic amino acids. Of the four heterologous pathways tested, *Francisella tularensis* and *Arabidopsis thaliana* were found to complement while *Chlamydia psittaci* did not (FIG. 5). Thus, this Example expands Example 2 to demonstrate approaches to determining which genes can and cannot complement the pertinent yeast strain.

Example 4

This example provides a demonstration that small molecule-mediated inhibition of heterologous pathways can be linked to a specific enzymatic activity or activities within the pathway.

Figure 6:
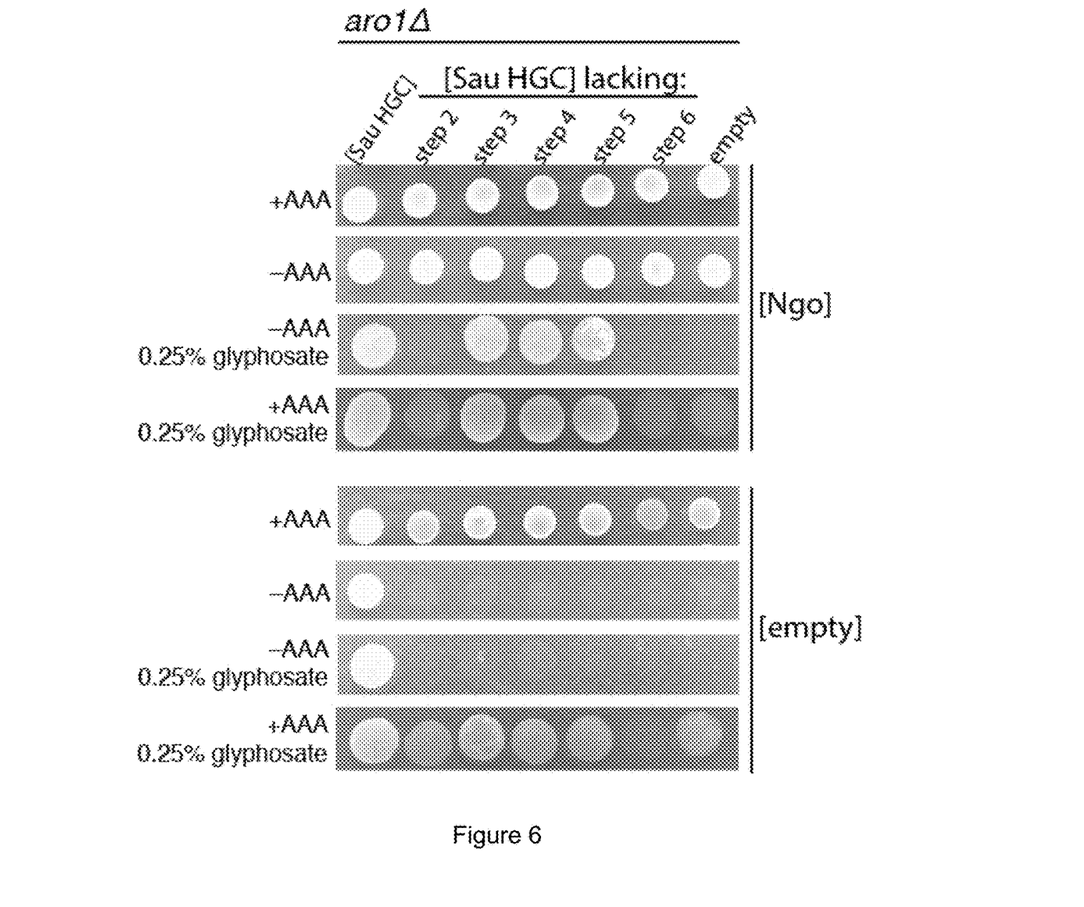

Glyphosate is a well-known inhibitor of the shikimate pathway (FIG. 3). The most widely recognized molecular target of glyphosate is the sixth step of the shikimate pathway, EPSPS enzymatic activity (FIG. 1) (7). Additional data shows that glyphosate also inhibits step 2 of the pathway, DHQS (25). To demonstrate that the molecular target of glyphosate can be determined for shikimate pathway yeast avatars, we used the N-1 assay described in example 2. The *Staphylococcus aureus* pathway, from which the N-1 constructs are derived, is resistant to glyphosate (FIG. 3). A pathway with demonstrated sensitivity, *Neisseria gonorrhoeae* (FIG. 3), was used to demonstrate identification of the molecular target of glyphosate. The set of N-1 constructs was transformed into aro1Δ yeast cells carrying either the *Neisseria gonorrhoeae* pathway or an empty vector. The resulting strains were spotted on medium with and without aromatic amino acids in the presence or absence of glyphosate (FIG. 6). This experiment demonstrated that the enzymatic activities of both step 2 (DHQS) and step 6 (EPSPS) of *Neisseria gonorrhoeae* are sensitive to glyphosate, since in the absence of *Staphylococcus aureus* pathway genes 2 and 6 ([Sau HGC] lacking step 2, step 6) cell growth was completely inhibited. More specifically, in these two cases, complementation was dependent on activity of *Neisseria gonorrhoeae* step 2 or step 6, and lack of growth is consistent with inhibition of these enzymes by glyphosate (FIG. 6).

REFERENCES (This listing is not an indication that any of the cited references are material to patentability):

1. R. Mir, S. Jallu, T. P. Singh, The shikimate pathway: review of amino acid sequence, function and threedimensional structures of the enzymes. *Crit Rev Microbiol* 41, 172-189 (2015).
2. M. Kanehisa, M. Furumichi, M. Tanabe, Y. Sato, K. Morishima, KEGG: new perspectives on genomes, pathways, diseases and drugs. *Nucleic Acids Res* 45, D353-D361 (2017).
3. K. Yang, G. Stracquadanio, J. Luo, J. D. Boeke, J. S. Bader, BioPartsBuilder: a synthetic biology tool for combinatorial assembly of biological parts. *Bioinformatics* 32, 937-939 (2016).
4. S. M. Richardson, P. W. Nunley, R. M. Yarrington, J. D. Boeke, J. S. Bader, GeneDesign 3.0 is an updated synthetic biology toolkit. *Nucleic acids research* 38, 2603-2606 (2010).
5. N. Agmon et al., Yeast Golden Gate (yGG) for the Efficient Assembly of *S. cerevisiae* Transcription Units. *ACS synthetic biology* 4, 853-859 (2015).
6. L. A. Mitchell et al., Versatile genetic assembly system (VEGAS) to assemble pathways for expression in *S. cerevisiae*. *Nucleic acids research* 43, 6620-6630 (2015).
7. T. Funke, H. Han, M. L. Healy-Fried, M. Fischer, E. Schonbrunn, Molecular basis for the herbicide resistance of Roundup Ready crops. *Proc Natl Acad Sci USA* 103, 13010-13015 (2006).
8. C. Gonzalez-Bello, Inhibition of Shikimate Kinase and Type II Dehydroquinase for Antibiotic Discovery: Structure-Based Design and Simulation Studies. *Curr Top Med Chem* 16, 960-977 (2016).
9. M. Izhar, L. DeSilva, H. S. Joysey, C. E. Hormaeche, Moderate immunodeficiency does not increase susceptibility to *Salmonella typhimurium* aroA live vaccines in mice. *Infect Immun* 58, 2258-2261 (1990).
10. G. A. McConkey, Targeting the shikimate pathway in the malaria parasite *Plasmodium falciparum*. *Antimicrob Agents Chemother* 43, 175-177 (1999).
11. B. Blanco et al., *Mycobacterium tuberculosis* shikimate kinase inhibitors: design and simulation studies of the catalytic turnover. *J Am Chem Soc* 135, 12366-12376 (2013).
12. N. I. Howard et al., Design and structural analysis of aromatic inhibitors of type II dehydroquinase from *Mycobacterium tuberculosis*. *ChemMedChem* 10, 116-133 (2015).

13. S. Gordon, J. Simithy, D. C. Goodwin, A. I. Calderon, Selective *Mycobacterium tuberculosis* Shikimate Kinase Inhibitors as Potential Antibacterials. *Perspect Medicin Chem* 7, 9-20 (2015).
14. M. Khanapur et al., *Mycobacterium tuberculosis* chorismate mutase: A potential target for TB. *Bioorg Med Chem*, (2017).
15. C. Avitia-Dominguez et al., Inhibition and biochemical characterization of methicillin-resistant *Staphylococcus aureus* shikimate dehydrogenase: an in silico and kinetic study. *Molecules* 19, 44914509 (2014).
16. V. F. Prazeres et al., Synthesis and biological evaluation of new nanomolar competitive inhibitors of *Helicobacter pylori* type II dehydroquinase. Structural details of the role of the aromatic moieties with essential residues. *J Med Chem* 53, 191-200 (2010).
17. V. W. Cheung et al., Identification of polyketide inhibitors targeting 3-dehydroquinate dehydratase in the shikimate pathway of *Enterococcus faecalis*. *PLoS One* 9, e103598 (2014).
18. A. Cersini, A. M. *Salvia*, M. L. Bernardini, Intracellular multiplication and virulence of *Shigella flexneri* auxotrophic mutants. *Infect Immun* 66, 549-557 (1998).
19. I. Charles, G. Dougan, Gene expression and the development of live enteric vaccines. *Trends Biotechnol* 8, 117-121 (1990).
20. G. Dougan, 1993 Colworth Prize Lecture. The molecular basis for the virulence of bacterial pathogens: implications for oral vaccine development. *Microbiology* 140 (Pt 2), 215-224 (1994).
21. M. J. Marsden, L. M. Vaughan, R. M. Fitzpatrick, T. J. Foster, C. J. Secombes, Potency testing of a live, genetically attenuated vaccine for salmonids. *Vaccine* 16, 1087-1094 (1998).
22. P. C. Scott, J. F. Markham, K. G. Whithear, Safety and efficacy of two live *Pasteurella multocida* aro-A mutant vaccines in chickens. *Avian Dis* 43, 83-88 (1999).
23. B. A. Stocker, Auxotrophic *Salmonella typhi* as live vaccine. *Vaccine* 6, 141-145 (1988).
24. J. Karlsson et al., Sequencing of the *Francisella tularensis* strain Schu 4 genome reveals the shikimate and purine metabolic pathways, targets for the construction of a rationally attenuated auxotrophic vaccine. *Microb Comp Genomics* 5, 25-39 (2000).
25. U. Roisch et al., The mechanism of action of the herbicide N-(phosphonomethyl)glycine: its effect on the growth and the enzymes of aromatic amino acid biosynthesis in *Escherichia coli. Hoppe Seylers Z Physiol Chem* 7, 1049-58 (1980).

While the invention has been described through specific embodiments, routine modifications will be apparent to those skilled in the art and such modifications are intended to be within the scope of the present invention.

What is claimed is:

1. A method for identification of a test agent that can inhibit one or more enzymes that are part of a shikimate pathway, the method comprising introducing the test agent into modified *Saccharomyces* yeast, the modified *Saccharomyces* yeast comprising:
   i) a disruption of an endogenous *Saccharomyces* yeast gene that encodes the shikimate pathway enzyme, and
   ii) a supplemental gene encoding a heterologous enzyme that is homologous to the enzyme encoded by the endogenous *Saccharomyces* yeast gene;
   wherein an inhibition of growth of the modified *Saccharomyces* yeast relative to a control is indicative that the test agent inhibits the shikimate pathway enzyme, and wherein the control comprises growth of the modified *Saccharomyces* yeast into which the test agent is introduced, and wherein the growth of the modified *Saccharomyces* yeast is performed on a medium that is supplemented with one or more aromatic amino acids such that growth of the modified yeast is independent of the function of the supplemental gene.

2. The method of claim 1, wherein a plurality of distinct test agents are introduced into a plurality of distinct *Saccharomyces* yeast cultures.

3. The method of claim 2, wherein the plurality of test agents are distinct test agents.

4. The method of claim 1, wherein the endogenous *Saccharomyces* yeast gene that is disrupted or deleted is ARO1.

5. The method of claim 1, wherein the supplemental gene is homologous to the endogenous *Saccharomyces* yeast gene that is disrupted or deleted and is from a species that is infectious to mammals, insects, birds, fish or plants.

6. The method of claim 1, wherein the supplemental gene is from a prokaryotic pathogen.

7. The method of claim 1, wherein the supplemental gene is from a eukaryotic pathogen.

* * * * *